(12) United States Patent
Tung

(10) Patent No.: US 8,552,008 B2
(45) Date of Patent: Oct. 8, 2013

(54) DEUTERATED 3-(DIHYDRO-1H-PYRAZOLO[4,3-D]PYRIMIDIN-5-YL)-4-PROPOXYBENZENESULFONAMIDE DERIVATIVES AND METHODS OF USE

(75) Inventor: Roger Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 512 days.

(21) Appl. No.: 11/876,754

(22) Filed: Oct. 22, 2007

(65) Prior Publication Data

US 2008/0188496 A1    Aug. 7, 2008

Related U.S. Application Data

(60) Provisional application No. 60/853,234, filed on Oct. 20, 2006.

(51) Int. Cl.
*C07D 487/04*    (2006.01)
*A61K 31/519*    (2006.01)
*A61P 15/10*    (2006.01)

(52) U.S. Cl.
USPC ........................... 514/262.1; 544/262

(58) Field of Classification Search
USPC ........................... 544/262; 514/262.1
See application file for complete search history.

(56) References Cited

U.S. PATENT DOCUMENTS

| | | | |
|---|---|---|---|
| 6,221,335 B1 * | 4/2001 | Foster | 424/1.81 |
| 6,440,710 B1 * | 8/2002 | Keinan et al. | 435/148 |
| 6,583,147 B1 | 6/2003 | Yoo et al. | |
| 6,603,008 B1 * | 8/2003 | Ando et al. | 546/269.7 |
| 7,517,990 B2 * | 4/2009 | Ito et al. | 546/184 |
| 2007/0082929 A1 * | 4/2007 | Gant et al. | 514/338 |
| 2007/0197695 A1 * | 8/2007 | Potyen et al. | 524/110 |
| 2008/0103122 A1 * | 5/2008 | Veltri | 514/210.02 |
| 2008/0280927 A1 | 11/2008 | Tung | |
| 2009/0197899 A1 | 8/2009 | Tung | |
| 2009/0270425 A1 | 10/2009 | Tung | |

FOREIGN PATENT DOCUMENTS

WO    WO-2007/016361    2/2007

OTHER PUBLICATIONS

Vippagunta et. al. (Advanced Drug Delivery Reviews, 2001, 48, pp. 3-26).*
Dyck, Journal of Neurochemistry vol. 46 Issue 2, pp. 399-404 (1986).*
Tonn Biological Mass Spectrometry vol. 22 Issue 11, pp. 633-642 (1993).*
Haskins, Biomedical Spectrometry vol. 9 Issue 7, pp. 269-277 (1982).*
Wolen, Journal of Clinical Pharmacology 1986; 26: 419-424.*
Browne, Journal of Clinical Pharmacology1998; 38:213-220.*
Baillie, Pharmacology Rev.1981; 33:81-132.*
Gouyette, Biomedical and Environmental Mass Spectrometry, vol. 15, 243-247 (1988).*
Cherrah, Biomedical and Environmental Mass Spectrometry vol. 14 Issue 11, pp. 653-657 (1987).*
Pieniaszek, J Clin Pharmacol.1999; 39:817-825.*
Honma et al., Drug Metab Dispos 15 (4): 551 (1987).*
U.S. Appl. No. 12/242,869, filed Sep. 20, 2008, Roger Tung.
Ji et al., "Role of human cytochrome P450 3A4 in the metabolism of DA-8159, a new erectogenic", Xenobiotica, Nov./Dec. 2004, vol. 34, No. 11/12, 973-982.
Foster et al., "Deuterium isotope effects in studies of drug metabolism", TIPS Dec. 1984, 524-527.
Kushner, et al., "Pharmacological uses and perspectives of heavy water and deuterated compounds", Can. J. Physiol. Pharmacol. 77: 79-88 (1999).
International Search Report and Written Opinion mailed Jul. 24, 2008, for corresponding PCT Application No. PCT/US07/82157.
Kang et al., "DA-8159 has erectile potentials much longer than the plasma half-life in a conscious rabbit model", Life Sciences, vol. 75, pp. 1075-1083, Jan. 1, 2004, XP002483948.
Extended European Search Report, dated Apr. 9, 2010, from corresponding European Patent Application No. 07 871 209.8.

(Continued)

*Primary Examiner* — Susanna Moore
(74) *Attorney, Agent, or Firm* — Edwards Wildman Palmer LLP; Jeffrey D. Hsi; Mark D. Russett

(57) ABSTRACT

This invention relates to novel 3-(dihydro-1H-pyrazolo[4,3-d]pyrimidin-5-yl)-4-propoxybenzenesulfonamide compounds of Formula I:

Formula (I)

wherein each Y is independently selected from hydrogen and deuterium and at least one Y is deuterium, as well as to pharmaceutically acceptable salts thereof. This invention also provides compositions comprising a compound of this invention and the use of such compositions in methods of treating diseases and conditions that are beneficially treated by administering inhibitors of cyclic guanosine 3',5'-monophosphate specific phosphodiesterase (cGMP-specific PDE), in particular PDE5.

4 Claims, No Drawings

(56) References Cited

OTHER PUBLICATIONS

Shim et al., "Pharmacokinetics of intravenous and oral DA-8159, a new erectogenic, in rats with protein-calorie malnutrition", J Pharm Pharmacol, vol. 56(12), pp. 1543-1550 (2004).
Shim et al., "Species Differences in the Formation of DA-8164 after Intravenous and/or Oral Administration of DA-8159, a New Erectogenic, to Mice, Rats, Rabbits, Dogs and Humans", Biopharmaceutics & Drug Disposition, vol. 26(4), pp. 161-166 (2005).
International Search Report and Written Opinion dated Apr. 3, 2009, in PCT Patent Application No. PCT/US09/00729.
Fisher et al., Current Opinion in Drug Discovery & Development 9:101-09 (2006).
Ling, K-HJ et al, Biochem Biophys Res Comm 1989, 160(2):844-49.
Jarman et al., "The deuterium isotope effect for the α-hydroxylation of tamoxifen by rat liver microsomes accounts for the reduced genotoxicity of [$D_5$-ethyl]tamoxifen", Carcinogenesis, vol. 16, No. 4, pp. 683-688, 1995.
Baker et al., "Inhibitory Effects of Deuterium Substitution on the Metabolism of Sevoflurane by the Rat", Drug Metabolism and Disposition, vol. 21, No. 6, pp. 1170-1171, 1993.
Spielmann et al., "Embroyotoxicity of Stable Isotopes and Use of Stable Isotopes in Studies of Teratogenetic Mechanisms", J Clin Pharmacol, 1986:26: 474-480.
van Beerendonk et al., "Genotoxicity of the flame retardant tris(2,3-dibromopropyl)phosphate in the rat and *Drosophila*: effects of deuterium substitution", Carcinogenesis, vol. 15, No. 6, pp. 1197-1202, 1994.
Van Langenhove, "Isotope Effects: Definitions and Consequences for Pharmacologic Studies", J Clin Pharmacol 26:383-389, 1986.
Wenzel, "Increased Brain Affinity of [131]Iodo-labelled N-(alkyl) Amphetamines following Deuteration", Journal of Labelled Compounds and Radiopharmaceuticals, vol. XXVII, No. 10 (in German with English translation), 1989.
Nelson et al., "Deuterium Isotope Effects on the Metabolism and Toxicity of Phenacetin in Hamsters", Drug Metabolism and Disposition, vol. 6, No. 4, pp. 363-367, 1978.
Foster, AB, Adv Drug Res 1985, 14:1-40.
Fukuto et al., "Determination of the Mechanism of Demethylenation of (Methylenedioxy) phenyl Compounds by Cytochrome P450 Using Deuterium Isotope Effects", J. Med. Chem, 1991, 34, 2871-2876.
Loftus et al., "Metabolism and Pharmacokinetics of Deuterium-Labelled Di-2-(Ethylhexyl) Adipate (DEHA) in Humans", Fd Chem. Toxic., vol. 31, No. 9, pp. 609-614, 1993.
Mabic et al., "Regioselective Synthesis of Deuterated Analogs of the Neurotoxin MPTP", Journal of Labelled Compounds and Radiopharmaceuticals, vol. XXXVIII, No. 3, pp. 255-262, 1996.
Nelson, "The Use of Stable and Radioactive Isoopes in Monitoring Reactive Metabolite Formation", in *Synthesis and Applications of Isotopically Labeled Compounds*. Proceedings of an International Symposium, Kansas City, MO, U.S.A., Jun. 6-11, 1982, pp. 89-94.
Scobie et al., "Labelled Compounds of Interest as Antitumour Agents. Part 4. Deuteration and Tritiation of a Nitrolmidazole-Carborane Designed for BNCT", Journal of Labelled Compounds and Radiopharmaceuticals, vol. XXXIV, No. 9, pp. 881-885, 1994.
Tsuzuki et al., "Ultrasound-Assisted Reduction of Cyanides to Deuteriated Aliphatic Amines", Journal of Labelled Compounds and Radiopharmaceuticals, vol. XXXVIII, No. 4, pp. 385-393, 1996.
Vandenheuvel, "The Use of Stable and Radioactive Isotopes in Drug Metabolism Studies", in *Syntheses and Applications of Isotopically Labeled Compounds*. Proceedings of an International Symposium, Kansas City, MO, U.S.A., Jun. 6-11, 1982, pp. 77-82.
Webb et al., "Labelled Compounds of Interest as Antitumour Agents. Part II (1). Synthesis of $^2$H and $^3$H Isotopomers of RSU 1069 and Ro 03-8799 (Pimonidazole)", Journal of Labelled Compounds and Radiopharmaceuticals, vol. XXVIII, No. 3, 1990, pp. 257-264.
Yang et al., "Synthesis of 3-Deuterated Diazepam and Nordiazepam 4-Oxides and Their Use in the Synthesis of Other 3-Deuterated Derivatives", Journal of Labelled Compounds and Radiopharmaceuticals, vol. XXXVIII, No. 8, 1996, pp. 753-759.
McCarty et al., "The Effects of Deuteration on the Metabolism of Halogenated Anesthetics in the Rat", Anesthesiology, 51:106-110, 1979.
Mazier et al., "Diet Fat Saturation and Feeding State Modulate Rates of Cholesterol Synthesis in Normolipidemic Men", J. Nutr., 127:332-340, 1997.
Mosberg et al, "Synthesis of Deuterium Labelled Penicillamine and Its Use for the Assignment of the $^1$H NMR Spectra of Two Cyclic Enkephalin Analogs", Journal of Labelled Compounds and Radiopharmaceuticals, vol. XXIV, No. 10, pp. 1265-1271, 1987.
Munro et al., "Plasma RRR-α-tocopherol concentrations are lower in smokers than in non-smokers after ingestion of a similar oral load of this antioxidant vitamin", Clinical Science (1997) 92, 87-93.
Avery et al., "Deuterated Antimalarials: Synthesis of Trideutero-Artemisinin, Dihydroartemisinin, and Arteether", Journal of Labelled Compounds and Radiopharmaceuticals, vol. XXXVIII, No. 3, pp. 249-254, 1996.
Castell et al., "A General Procedure for Isotopic (Deuterium) Labelling of Non-Steroidal Antiinflammatory 2-Arylpropionic Acids", Journal of Labelled Compounds and Radiopharmaceuticals, vol. XXXIV, No. 1, pp. 93-100, 1994.
Ferraboschi et al., "A Facile Synthesis of Pentadeuterated Domiodol (2-Iodomethyl-4-Hydroxymethyl-1,3-Dioxolane) From Glycerol-1,1,2,3,3-$d_5$", Journal of Labelled Compounds and Radiopharmaceuticals, vol. XXXIV, No. 3, pp. 303-306, 1994.
Hinz et al., "Stabilities of $^3$H- and $^2$H-labelled Camptothecins", Journal of Labelled Compounds and Radiopharmaceuticals, vol. XXXVIII, No. 8, pp. 733-742, 1996.
Silvestro, et al., "Human Pharmacokinetics of Glycosaminoglycans Using Deuterium-Labeled and Unlabeled Substances: Evidence for Oral Absorption", Seminars in Thrombosis and Hemostasis, vol. 20, No. 3, pp. 281-292, 1994.

\* cited by examiner

DEUTERATED 3-(DIHYDRO-1H-PYRAZOLO[4,3-D]PYRIMIDIN-5-YL)-4-PROPOXYBENZENESULFONAMIDE DERIVATIVES AND METHODS OF USE

RELATED APPLICATIONS

This application claims the benefit of U.S. provisional patent application No. 60/853,234, filed Oct. 20, 2006, the contents of which are incorporated herein by reference.

This invention relates to novel 3-(dihydro-1H-pyrazolo[4,3-d]pyrimidin-5-yl)-4-propoxybenzenesulfonamide compounds, their derivatives, pharmaceutically acceptable salts, solvates, and hydrates thereof. This invention also provides compositions comprising a compound of this invention and the use of such compositions in methods of treating diseases and conditions that are beneficially treated by administering inhibitors of cyclic guanosine 3',5'-monophosphate specific phosphodiesterase (cGMP-specific PDE), in particular PDE5.

Udenafil, also known variously as 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide, and as 3-(1-methyl-7-oxo-3-propyl-3a,6,7,7a-tetrahydro-1H-pyrazolo[4,3-d]pyrimidin-5-yl)-N-(2-(1-methylpyrrolidin-2-yl)ethyl)-4-propoxybenzenesulfonamide, modulates activity of the cyclic guanosine monophosphate-specific phosphodiesterase type 5 (PDE5).

Udenafil has been clinically demonstrated to be an effective agent for erectile dysfunction and is currently approved for marketing in South Korea for the treatment of impotence.

Udenafil undergoes hepatic metabolism in humans, with sulfonamide N-dealkyation by cytochrome P450 3A4 (CYP3A4) being responsible for formation of the predominantly-observed circulating metabolite. Analogously with rats and dogs, additional oxidation may occur, resulting in side-chain hydroxylation and pyrazole N-dealkylation.

Side effects reportedly associated with udenafil include were mild to moderate facial flushing and headache. In addition, other PDE5 inhibitors have been associated with possible vision problems.

Despite the beneficial activities of udenafil, there is a continuing need for new compounds to treat the aforementioned diseases and conditions.

DEFINITIONS

The terms "ameliorate" and "treat" are used interchangeably and include both therapeutic and prophylactic treatment. Both terms mean decrease, suppress, attenuate, diminish, arrest, or stabilize the development or progression of a disease (e.g., a disease or disorder delineated herein).

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of udenafil will inherently contain small amounts of deuterated and/or $^{13}C$-containing isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66:15; Ganes L Z et al., Comp Biochem Physiol Mol Integr Physiol 1998, 119:725. In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3000 (45% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

The term "isotopologue" refers to a species that differs from a specific compound of this invention only in the isotopic composition thereof.

The term "compound," as used herein, is also intended to include any salts, solvates or hydrates thereof.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention will include both racemic mixtures, and also individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X" % of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

Both "²H" and "D" refer to deuterium.

"Stereoisomer" refers to both enantiomers and diastereomers.

"Tert", "ᵗ", and "t-" each refer to tertiary.

"US" refers to the United States of America.

"FDA" refers to Food and Drug Administration.

"NDA" refers to New Drug Application.

Throughout this specification, a variable may be referred to generally (e.g., "each R") or may be referred to specifically (e.g., R¹, R², R³, etc.). Unless otherwise indicated, when a variable is referred to generally, it is meant to include all specific embodiments of that particular variable.

Therapeutic Compounds

The present invention provides a compound of Formula I:

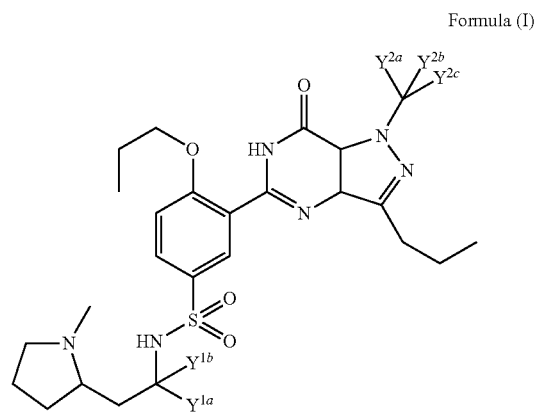

Formula (I)

or a salt (e.g., a pharmaceutically acceptable salt) thereof; or a hydrate or solvate thereof; wherein:

each Y (including $Y^{1a}, Y^{1b}, Y^{2a}, Y^{2b}$, and $Y^{2c}$, where applicable) is independently $^2H$ or $^1H$; provided that at least one Y is $^2H$.

A preferred embodiment is the compound wherein both $Y^{1a}$ and $Y^{1b}$ are $^2H$.

Another embodiment is that wherein $Y^{2a}, Y^{2b}$, and $Y^{2c}$ are each $^2H$.

Another embodiment is that wherein all Y are $^2H$.

In yet another embodiment, the compound is selected from any one of the compounds set forth in Table 1 (below):

TABLE 1

Table 1: Exemplary Compounds of Formula I

| Compound | $Y^{1a}$ | $Y^{1b}$ | $Y^{2a}$ | $Y^{2b}$ | $Y^{2c}$ |
|---|---|---|---|---|---|
| 100 | D | D | D | D | D |
| 101 | D | D | H | D | H |
| 102 | D | D | D | H | D |
| 103 | D | D | H | H | H |
| 104 | D | H | D | D | D |
| 105 | D | H | H | D | H |
| 106 | D | H | D | H | D |
| 107 | D | H | H | H | H |
| 108 | H | H | D | D | D |
| 109 | H | H | H | D | H |
| 110 | H | H | D | H | D |

In another set of embodiments, any atom not designated as deuterium in any of the embodiments set forth above is present at its natural isotopic abundance.

The synthesis of compounds of Formula I can be readily achieved by synthetic chemists of ordinary skill. Relevant procedures and intermediates are disclosed, for instance in U.S. Pat. Nos. 6,583,147 and 6,844,436.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Certain intermediates can be used with or without purification (e.g., filtration, distillation, sublimation, crystallization, trituration, solid phase extraction, and chromatography).

EXEMPLARY SYNTHESIS

A convenient method for synthesizing 3-(dihydro-1H-pyrazolo[4,3-d]pyrimidin-5-yl)-4-propoxybenzenesulfonamide compounds of Formula I is depicted in Scheme 1.

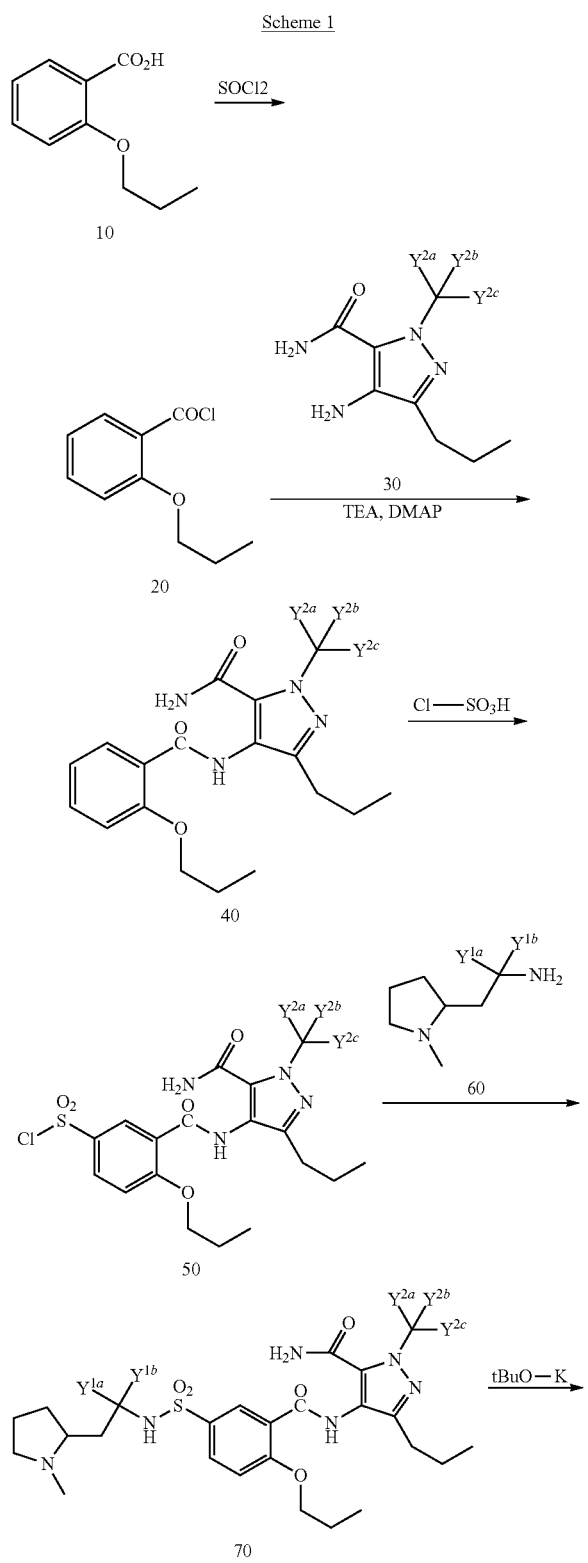

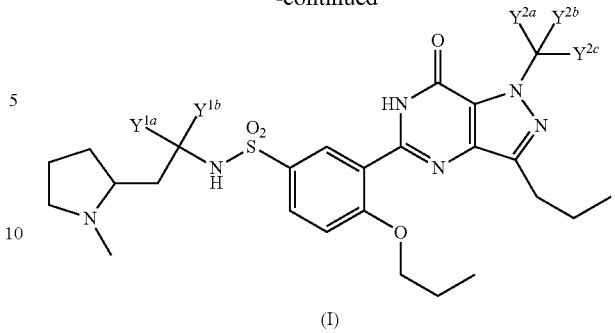

As shown in Scheme 1, in an exemplary synthesis, acid 10 is converted to acid chloride 20 and then reacted with amine 30 under amidation conditions (e.g., triethylamine (TEA), dimethylaminopyridine (DMAP)) to produce amide 40. Sulfonation of 40 with chlorosulfonic acid to produce sulfonyl chloride 50 is followed by reaction with amine 60 (e.g., in dichloromethane) to produce compound 70. Base-promoted ring closure (e.g., in refluxing t-butanol with potassium t-butoxide) then provides a compound of Formula I.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art. Additional methods of synthesizing compounds of Formula I and their synthetic precursors, including those within routes not explicitly shown in schemes herein, are within the means of chemists of ordinary skill in the art. Methods for optimizing reaction conditions and, if necessary, minimizing competing by-products, are known in the art. In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier MDL), or internet search engines such as Google® or keyword databases such as the US Patent and Trademark Office text database.

The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3rd Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of Formula I (e.g., including any of the formulae herein), or a pharmaceutically acceptable salt, solvate, or hydrate of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added.

For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as udenafil, i.e., any compound or therapeutic agent known to have or that demonstrates advantageous properties when administered with a PDE5 inhibitor compound. Such agents include those indicated as being useful in combination with a PDE5 inhibitor compound, or more particularly, udenafil.

Preferably, the second therapeutic agent is an agent useful in the treatment or prevention of a disease or condition selected from erectile dysfunction, benign prostatic hyperplasia, and pulmonary arterial hypertension. Exemplary second agents include angiotensin converting enzyme (ACE) inhibitors and angiotensin II receptor antagonists.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 50 mg to about 150 mg, or from about 10 mg to about 300 mg, or from about 5 mg to about 500 mg, or from about 1 mg to about 1000 mg.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for udenafil.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of modulating the activity of PDE5 in a cell, comprising contacting a cell with one or more compounds of Formula I herein.

According to another embodiment, the invention provides a method of treating a patient suffering from, or susceptible to, a disease that is beneficially treated by udenafil comprising the step of administering to said patient an effective amount of a compound or a composition of this invention. Such diseases include, but are not limited to erectile dysfunction, benign prostatic hyperplasia, and pulmonary arterial hypertension.

In one particular embodiment, the method of this invention is used to treat a patient suffering from or susceptible to a disease or condition selected from erectile dysfunction, benign prostatic hyperplasia, and pulmonary arterial hypertension.

In another particular embodiment, the method of this invention is used to treat a patient suffering from or susceptible to erectile dysfunction.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with a PDE5 inhibitor, more particularly udenafil. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I and a second therapeutic agent for treatment of the following conditions: erectile dysfunction, benign prostatic hyperplasia, and pulmonary arterial hypertension.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I for use in the treatment or prevention in a patient of a disease, disorder or symptom thereof delineated herein.

Diagnostic Methods and Kits

The compounds and compositions of this invention are also useful as reagents in methods for determining the concentration of udenafil in solution or biological sample such as plasma, examining the metabolism of udenafil and other analytical studies.

According to one embodiment, the invention provides a method of determining the concentration, in a solution or a biological sample, of udenafil, comprising the steps of:
a) adding a known concentration of a compound of Formula I to the solution of biological sample;
b) subjecting the solution or biological sample to a measuring device that distinguishes udenafil from a compound of Formula I;
c) calibrating the measuring device to correlate the detected quantity of the compound of Formula I with the known concentration of the compound of Formula I added to the biological sample or solution; and
d) measuring the quantity of udenafil in the biological sample with said calibrated measuring device; and
e) determining the concentration of udenafil in the solution of sample using the correlation between detected quantity and concentration obtained for a compound of Formula I.

Measuring devices that can distinguish udenafil from the corresponding compound of Formula I include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula I comprising the steps of contacting the compound of Formula I with a metabolizing enzyme source for a period of time and comparing the amount of the compound of Formula I with the metabolic products of the compound of Formula I after the period of time.

In a related embodiment, the invention provides a method of evaluating the metabolic stability of a compound of Formula I in a patient following administration of the compound of Formula I. This method comprises the steps of obtaining a serum, urine or feces sample from the patient at a period of time following the administration of the compound of Formula I to the subject; and comparing the amount of the compound of Formula I with the metabolic products of the compound of Formula I in the serum, urine or feces sample.

The present invention also provides kits for use to treat erectile dysfunction, benign prostatic hyperplasia, and pulmonary arterial hypertension. These kits comprise (a) a pharmaceutical composition comprising a compound of Formula I or a salt, hydrate, or solvate thereof, wherein said pharmaceutical composition is in a container; and (b) instructions describing a method of using the pharmaceutical composition to treat erectile dysfunction, benign prostatic hyperplasia, or pulmonary arterial hypertension.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

Evaluation of Metabolic Stability

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., PharmRes, 1997, 14:152.

Microsomal Assay: The metabolic stability of compounds of Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Experimental Procedures: Human liver microsomes are obtained from a commercial source (e.g., Absorption Systems L.P. (Exton, Pa.)). The incubation mixtures are prepared as follows:

Reaction Mixture Composition

| Liver Microsomes | 1.0 mg/mL |
| --- | --- |
| NADPH | 1 mM |
| Potassium Phosphate, pH 7.4 | 100 mM |
| Magnesium Chloride | 10 mM |
| Test Compound | 1 µM. |

Incubation of Test Compounds with Liver Microsomes: The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 µM. An aliquot of the reaction mixture is prepared as a blank control, by the addition of plain organic solvent (not the test compound). The reaction is initiated by the addition of cofactors (not into the negative controls), and then incubated in a shaking water bath at 37° C. Aliquots (200 µL) are withdrawn in triplicate at multiple time points (e.g., 0, 15, 30, 60, and 120 minutes) and combined with 800 µL of ice-cold 50/50 acetonitrile/dH$_2$O to terminate the reaction. The positive controls, testosterone and propranolol, as well as udenafil, are each run simultaneously with the test compounds in separate reactions.

All samples are analyzed using LC-MS (or MS/MS). An LC-MRM-MS/MS method is used for metabolic stability. Also, Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

SUPERSOMES™ Assay. Various human cytochrome P450-specific SUPERSOMES™ are purchased from Gentest (Woburn, Mass., USA). A 1.0 mL reaction mixture containing 25 pmole of SUPERSOMES™, 2.0 mM NADPH, 3.0 mM MgCl, and 1 µM of a compound of Formula I or II in 100 mM potassium phosphate buffer (pH 7.4) was incubated at 37° C. in triplicate. Positive controls contain 1 µM of udenafil instead of a compound of formula I. Negative controls used Control Insect Cell Cytosol (insect cell microsomes that lacked any human metabolic enzyme) purchased from GenTest (Woburn, Mass., USA). Aliquots (50 µL) are removed from each sample and placed in wells of a multi-well plate at various time points (e.g., 0, 2, 5, 7, 12, 20, and 30 minutes) and to each aliquot is added 50 µL of ice cold acetonitrile with 3 µM haloperidol as an internal standard to stop the reaction.

Plates containing the removed aliquots are placed in −20° C. freezer for 15 minutes to cool. After cooling, 100 µL of deionized water is added to all wells in the plate. Plates are then spun in the centrifuge for 10 minutes at 3000 rpm. A portion of the supernatant (100 μL) is then removed, placed in a new plate and analyzed using Mass Spectrometry.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

I claim:
1. A compound of Formula I:

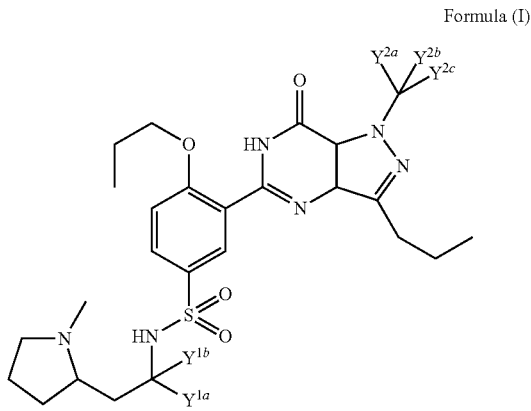

Formula (I)

or a salt thereof; wherein:

each of $Y^{1a}, Y^{1b}, Y^{2a}, Y^{2b}$, and $Y^{2c}$ is independently $^2H$ or $^1H$; provided that at least one Y is $^2H$, wherein the compound is selected from the group consisting of Compound 100, Compound 103 and Compound 108, as set forth in the table below:

| Compound | $Y^{1a}$ | $Y^{1b}$ | $Y^{2a}$ | $Y^{2b}$ | $Y^{2c}$ |
|---|---|---|---|---|---|
| 100 | D | D | D | D | D |
| 103 | D | D | H | H | H |
| 108 | H | H | D | D | D | and wherein a position on the compound designated as having deuterium has a minimum isotopic enrichment factor of at least 3000 (45% deuterium incorporation).

2. The compound of claim 1, wherein any atom not designated as deuterium is present at its natural isotopic abundance.

3. A pyrogen-free composition comprising:
a compound of claim 1, or a pharmaceutically acceptable salt thereof; and
an acceptable carrier.

4. The composition of claim 3, wherein the composition is formulated for pharmaceutical administration and the carrier is a pharmaceutically acceptable carrier.

* * * * *